United States Patent [19]

Saito et al.

[11] Patent Number: 4,822,882
[45] Date of Patent: Apr. 18, 1989

[54] DC-52 DERIVATIVES AND THEIR ANTITUMOR USE

[75] Inventors: Hiromitsu Saito, Sagamihara; Yoichi Uosaki; Akira Sato, both of Machida; Tadashi Hirata, Yokohama; Makoto Morimoto, Shizuoka; Tadashi Ashizawa, Numazu, all of Japan

[73] Assignee: Kyowa Hakko Kogyo Co., Ltd., Tokyo, Japan

[21] Appl. No.: 102,359

[22] Filed: Sep. 29, 1987

[30] Foreign Application Priority Data

Oct. 3, 1986 [JP] Japan .................................. 235858
Dec. 2, 1986 [JP] Japan .................................. 287212
Aug. 20, 1987 [JP] Japan .................................. 207180

[51] Int. Cl.$^4$ ................. A61K 31/495; C07D 498/22; C07D 487/18
[52] U.S. Cl. ................................... 544/342; 544/343
[58] Field of Search ............................... 544/342, 343

[56] References Cited

U.S. PATENT DOCUMENTS 4,650,869 3/1987 Hirata .................................. 544/343

FOREIGN PATENT DOCUMENTS 0157126 10/1985 European Pat. Off. .

OTHER PUBLICATIONS

Chem. Abs., vol. 98, No. 11 (1983), 87622z, Kyowa, Ltd.

Primary Examiner—Mark L. Berch
Attorney, Agent, or Firm—Fitzpatrick, Cella, Harper & Scinto

[57] ABSTRACT

Compounds represented by the following formula or by the corresponding hydroquinone type formula:

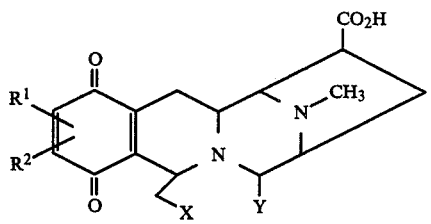

in which $R^1$ and $R^2$ are independently hydrogen, lower alkoxy, azido, amino, lower alkylamino, di-lower alkylamino, cyclic amino, lower alkylthio or unsubstituted or substituted arylthio; and X represents hydroxyl and Y represents cyano or X and Y together represents —O— in the form of —X—Y—, have an excellent antitumor activity.

2 Claims, No Drawings

DC-52 DERIVATIVES AND THEIR ANTITUMOR USE

BACKGROUND OF THE INVENTION

The present invention relates to novel antitumor compounds.

DC-52 is an antibiotic represented by the following formula and has an antitumor activity against lymphocytic leukemia P388, etc. as well as an antibacterial activity against various bacteria (Japanese Published Unexamined Patent Application No. 170189/82).

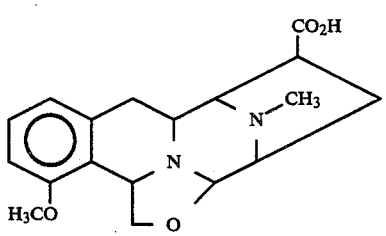

Further, DX-52-1 which is a derivative of DC-52 and which is represented by the following formula is known to have an antitumor activity (Japanese Published Unexamined Patent Application No. 210086/84, which corresponds to U.S. Pat. No. 4,650,869, issued Mar. 17, 1987).

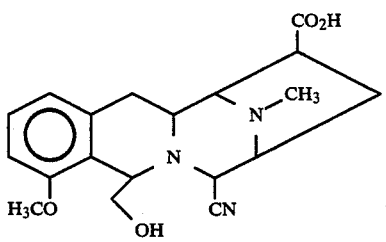

DC-52 derivatives which have more excellent antitumor activity are always in demand as well as other antitumor antibiotics.

SUMMARY OF THE INVENTION

In accordance with the present invention, the compounds which have an excellent antitumor activity are represented by the following formula (I) or by the corresponding hydroquinone type formula:

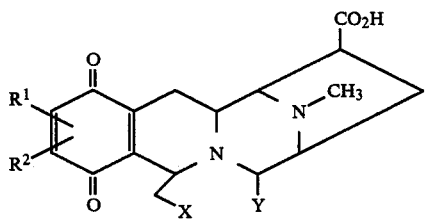

in which $R^1$ and $R^2$ are independently hydrogen, lower alkoxy, azido, amino, lower alkylamino, di-lower alkylamino, cyclic amino, lower alkylthio or unsubstituted or substituted arylthio; and X represents hydroxyl and Y represents cyano or X and Y together represent —O— in the form of —X—Y—. [The compounds are hereinafter referred to as Compounds (I). The same shall apply hereinafter to the numbering of compounds.]

DETAILED DESCRIPTION OF THE INVENTION

In the definitions of $R^1$ and $R^2$ in the formula (I), the lower alkoxy is preferably an alkoxy group having 1 to 4 carbon atoms such as methoxy, ethoxy, i-propoxy, n-propoxy, n-butoxy, etc.; the lower alkylamino is preferably an alkylamino group having 1 to 3 carbon atoms such as methylamino, propylamino, etc.; the di-lower alkylamino is preferably a dialkylamino group having 1 to 3 carbon atoms such as dimethylamino, diethylamino, etc.; the cyclic amino is preferably a cyclic amino group having 3 to 6 ring members such as aziridino, azetidino, pyrrolidino, piperidino, etc.; the lower alkylthio is preferably an alkylthio group having 1 to 4 carbon atoms such as methylthio, ethylthio, n-propylthio, i-propylthio, n-butylthio, etc.; and the unsubstituted or substituted arylthio includes phenylthio, p-fluorophenylthio, p-methoxyphenylthio, etc.

Pharmaceutically acceptable salts of Compounds (I) and the corresponding hydroquinone forms also have an excellent antitumor activity, as well as Compounds (I) and the hydroquinone forms thereof. The salts include pharmaceutically acceptable acid-addition salts, alkali metal salts, alkaline earth metal salts and ammonium salts as well as pharmaceutically acceptable organic base-addition salts. The pharmaceutically acceptable acid-addition salts include pharmaceutically acceptable inorganic acid-addition salts such as hydrochloride, hydrobromide, hydroiodide, sulfate, phosphate, nitrate, etc., and pharmaceutically acceptable organic acid-addition salts such as acetate, benzoate, maleate, fumarate, succinate, tartrate, citrate, oxalate, glyoxalate, aspartate, methanesulfonate, ethanesulfonate, propanesulfonate, methane-disulfonate, α,β-ethanedisulfonate, benzenesulfonate, etc. The alkali metal salts include sodium salt, potassium salt, etc.; and the alkaline earth metal salts include calcium salt, magnesium salt, etc. The pharmaceutically acceptable organic base-addition salts include ethanolamine-, triethylamine-, morpholine- and piperidine-addition salts, etc.

Processes for the preparation of Compounds (I) and the hydroquinone forms thereof are explained below.

Compounds (I) and the hydroquinone forms thereof can be prepared in accordance with the following steps, wherein Compounds (I-1), (I-2), etc. are included in the scope of the definition of Compound (I).

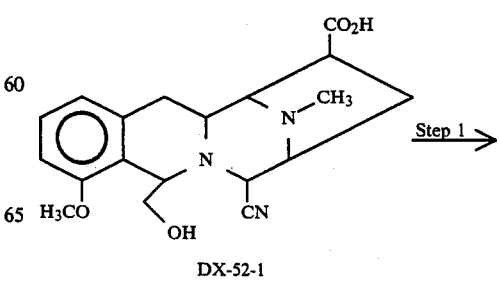

DX-52-1

-continued

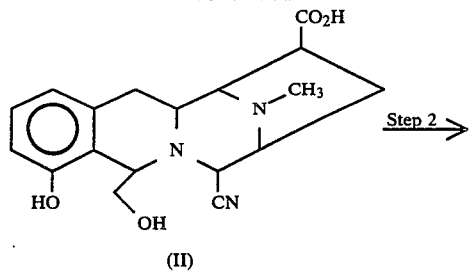
(II)

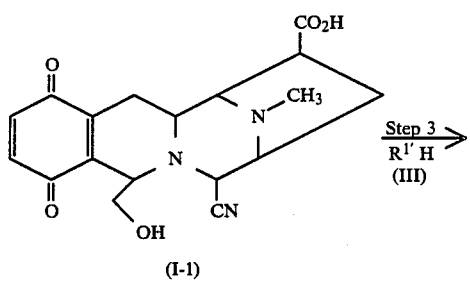
(I-1)

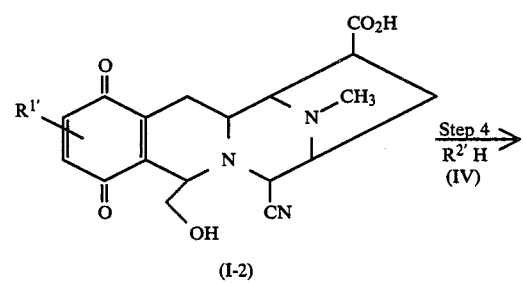
(I-2)

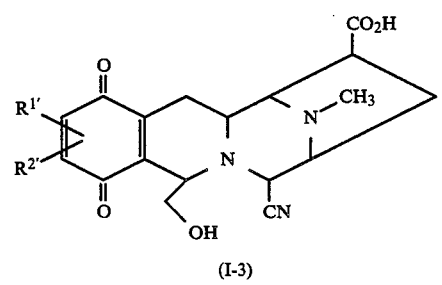
(I-3)

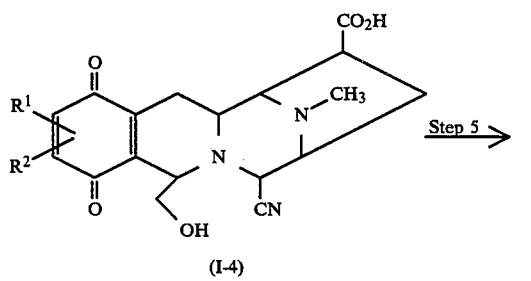
(I-4)

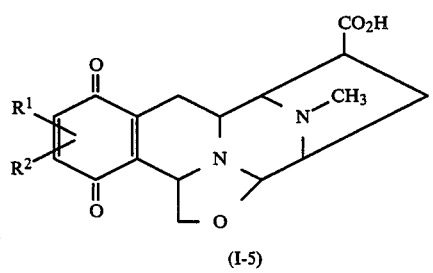
(I-5)

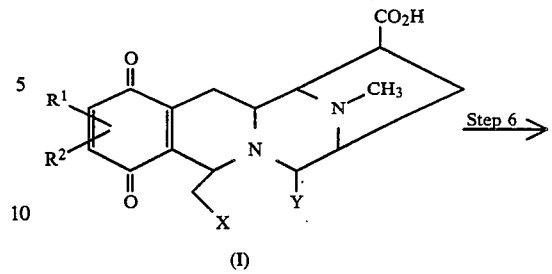
(I)

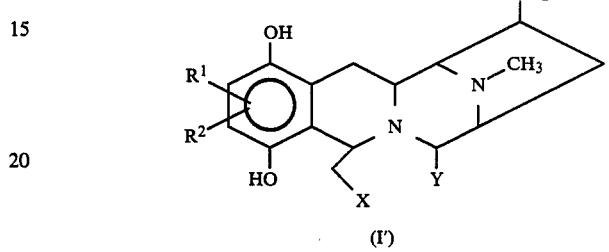
(I')

In these formulae, $R^{1'}$ and $R^{2'}$ are the same as $R^1$ and $R^2$, respectively, except hydrogen; and $R^1$, $R^2$, X and Y have the same meanings as in the formula (I). Compounds (I-4) include Compounds (I-1), (I-2) and (I-3); Compounds (I) include Compounds (I-4) and (I-5); and Compounds (I') are hydroquinone type compounds corresponding to Compounds (I).

Step 1

First, DX-52-1 is reacted with a demethylating agent in an inert solvent, and then the reaction mixture is poured into ice water to obtain Compound (II). The demethylating agent includes boron tribromide, boron trichloride, aluminium chloride-ethanethiol, etc. and is used, in general, in an amount of 3 to 7 equivalents to DX-52-1. The inert solvent includes halogenated alkanes such as methylene chloride, chloroform, etc., and aromatic hydrocarbons such as toluene, etc. The reaction is generally carried out at −78° to 30° C. and is completed in several hours to 2 days. After the reaction, the reaction mixture is poured into ice water, and after the pH of the aqueous layer is adjusted to 6.5 to 7.5, sodium cyanide is added thereto. The resulting aqueous layer is isolated, concentrated and then subjected to column chromatography to obtain Compound (II).

Step 2

Compound (II) is oxidized with Fremy's salt (potassium nitrosodisulfonate) in an inert solvent to obtain Compound (I-1). Fremy's salt is used, in general, in an amount of 2 to 5 equivalents to Compound (II).

As the inert solvent, a mixed solvent comprising an organic solvent such as acetonitrile, methanol, ethanol, tetrahydrofuran, dioxane, dimethoxyethane, etc. and water is used. The reaction is usually carried out at room temperature for 1 to 10 hours. Purification can be effected by column chromatography or HPLC.

Step 3

This step actually proceeds in accordance with the following two-step reaction.

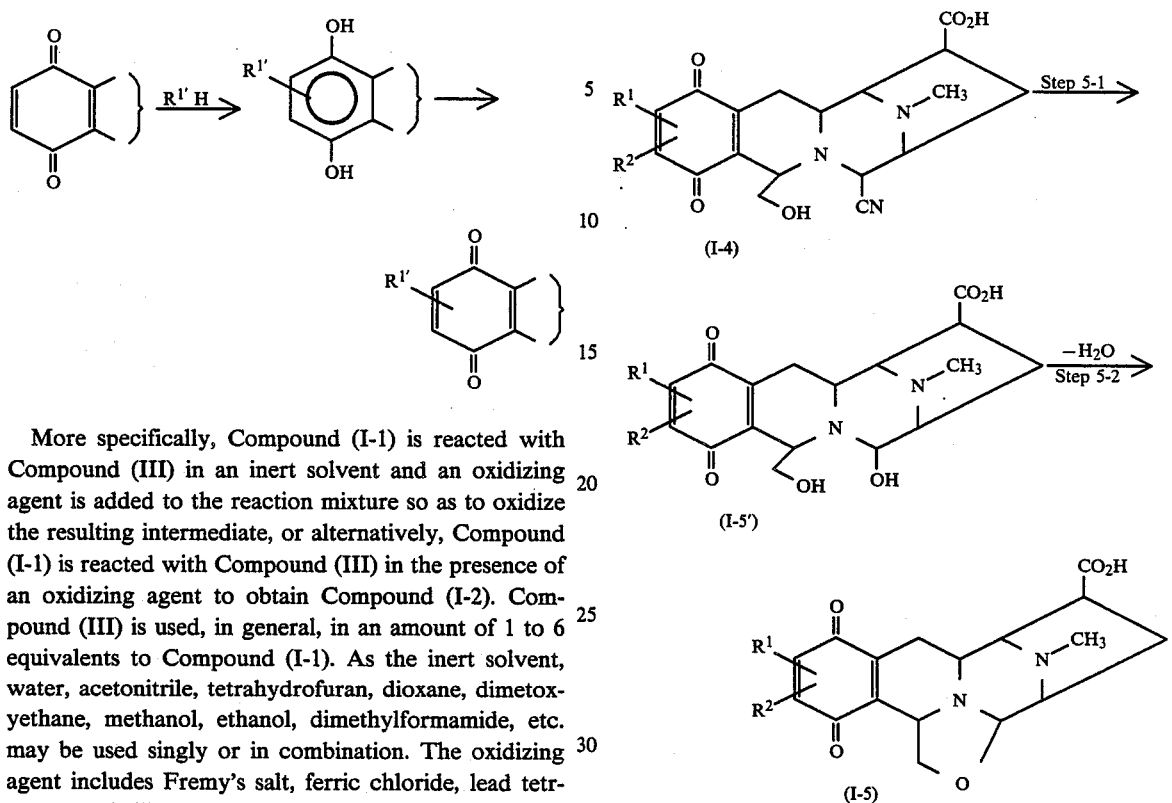

More specifically, Compound (I-1) is reacted with Compound (III) in an inert solvent and an oxidizing agent is added to the reaction mixture so as to oxidize the resulting intermediate, or alternatively, Compound (I-1) is reacted with Compound (III) in the presence of an oxidizing agent to obtain Compound (I-2). Compound (III) is used, in general, in an amount of 1 to 6 equivalents to Compound (I-1). As the inert solvent, water, acetonitrile, tetrahydrofuran, dioxane, dimetoxyethane, methanol, ethanol, dimethylformamide, etc. may be used singly or in combination. The oxidizing agent includes Fremy's salt, ferric chloride, lead tetraacetate, thallium (III) trifluoroacetate, ammonium cerium (IV) nitrate, oxygen, cupric acetate, etc., and is used, in general, in an amount of 1 to 3 equivalents to Compound (I-1). In the case where the intermediate is oxidized following the reaction of Compound (I-1) and Compound (III), the first reaction is generally carried out at $-10°$ to 30° C. for 30 minutes to 3 hours, and the following oxidization reaction is generally carried out at the same temperature for 30 minutes to 4 hours. On the other hand, in the case where Compound (I-1) is reacted with Compound (III) under oxidizing conditions, the reaction is generally carried out at $-10°$ to 50° C. for 1 hour to 15 days.

After the reaction, a buffer having pH of 3 to 4 is added to the reaction mixture and the resulting mixture is concentrated under reduced pressure, or alternatively, the reaction mixture is extracted with a water-insoluble solvent such as chloroform, ethyl acetate, etc., and washed with a saturated sodium chloride solution, and thereafter the resulting extract is concentrated and then purified. The purification can be effected by column chromatography, TLC, HPLC, etc.

Step 4

Compound (I-2) is reacted with Compound (IV) in the same manner as in Step 3 to obtain Compound (I-3). Purification can also be effected in the same manner.

Step 5

This step proceeds in accordance with the following two-step reaction.

Compound (I-4) is first kept in water or a hydrophilic solvent in the presence of a silver salt to give Compound (I-5').

The hydrophilic solvent includes acetonitrile, methanol, ethanol, tetrahydrofuran, dioxane, etc., and can be used singly or in combination. The silver salt includes silver nitrate, silver chlorate, silver perchlorate, silver fluoride, etc. Although the amount of the silver salt to be used is, in general, one equivalent to Compound (I-4) in which X is hydroxyl and Y is cyano, the salt can be used excessively in an amount of up to 3 equivalents so as to shorten the reaction time and to improve the yield of Compound (I-5'). The reaction is generally carried out at 0° to 30° C. and is finished in 30 minutes to several hours.

After the reaction, the reaction mixture is filtered, concentrated, and then purified by column chromatography, TLC, HPLC, etc.

Compound (I-5') is dried, whereby it is converted into Compound (I-5) by intramolecular dehydration.

Step 6

Compound (I) is subjected to catalytic hydrogenation in an inert solvent to give Compound (I'). The catalyst to be used in this reaction includes Pd-C, PtO$_2$, etc. The catalyst is used in an amount of 20 to 40% (w/w) of Compound (I). As the inert solvent, water, methanol, ethanol, acetonitrile, tetrahydrofuran, acetic acid, etc. may be used singly or in combination. The reaction is generally carried out at 0° to 40° C. and is finished in 15 minutes to 3 hours.

Step 7 (Alternative Method)

As an alternative to the above-mentioned procedures, the carboxyl group of Compound (II) may be subjected to esterification and then the same treatment as in the above-mentioned steps 2 through 6, followed by de-esterification, to obtain Compound (I) or (I'). By the adoption of such process, smooth progress of the reaction, improvement of the yield and facilitation of the isolation and purification can sometimes be attained. Specifically, Compound (II) is first reacted with diphenyldiazomethane in an inert solvent to obtain a compound represented by the formula (II'):

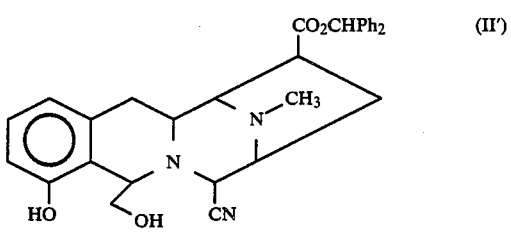

The diphenyldiazomethane is generally used in an amount of 1 to 4 equivalents to Compound (II). As the inert solvent, chloroform, methylene chloride, methanol, ethanol, tetrahydrofuran, etc. may be used singly or in combination.

The reaction is generally carried out at room temperature and is finished in one to several hours. The purification is effected by chromatography or recrystallization. On the other hand, the diphenylmethylester of Compounds (I) and (I') can be converted into Compounds (I) and (I'), respectively by general acid hydrolysis. Such a method is described, for example, in Green's *Protective Groups in Organic Synthesis*, 174 (1981) (by John Willey & Sons, Incorporated). Preferably, the diphenylmethylester of Compound (I) or (I') is reacted with trifluoroacetic acid with no solvent or in an inert solvent to obtain Compound (I) or (I'). The inert solvent includes methylene chloride, toluene, etc. The trifluoroacetic acid is suitably used in an amount of 5 to 100 equivalents to the starting compound. When the present reaction is carried out in the presence of 1 to 50 equivalents of anisol, phenol, hydroquinone, ethanethiol, etc. to the starting compound, it is possible to prevent the formation of undesirable by-products. The reaction is generally carried out at 0° C. to room temperature and is finished in 30 minutes to 8 hours.

After the completion of reaction, the reaction mixture is concentrated and then purified by column chromatography, HPLC, etc. Alternatively, after the reaction mixture is concentrated, a buffer with pH 4 is added thereto, the resulting mixture is treated with a water-insoluble solvent such as chloroform, ethyl acetate, etc. to extract Compound (I) or (I'), and then the resulting extract is, after being concentrated, purified by column chromatography, HPLC, etc.

Compounds (I), the corresponding hydroquinone forms and their pharmaceutically acceptable salts have a strong antitumor activity against lymphocytic leukemia P388, etc., and therefore are believed to be useful as antitumor agents for mammals including human beings. Among such compounds of the present invention, those of the formula (I) wherein $R^1$ and $R^2$ are the same or different lower alkylthio, X is hydroxyl and Y is cyano, or X and Y together represent —O— in the form of —X—Y—, as well as their pharmaceutically acceptable salts, are especially excellent in antitumor activity.

The pharmaceutical activity of Compounds (I) is explained below by reference to experimental example.

EXPERIMENTAL EXAMPLE 1

Antitumor Activity

The antitumor activity of some typical Compounds (I) against lymphocytic leukemia P388 is shown in Table 1.

TABLE 1

| Compound | Dose (mg/kg) | T/C (%) |
|---|---|---|
| 2 | 12.5 | 153 |
| 3 | 6.25 | 148 |
| 4 | 12.5 | 150 |
| 9 | 25 | 132 |
| 11 | 3.13 | 120 |
| 15 | 6.25 | 147 |
| 16 | 12.5 | 165 |
| 17 | 6.25 | 149 |
| 18 | 6.25 | 164 |
| 19 | 25 | 156 |
| 20 | 12.5 | 158 |
| 21 | 25 | 165 |
| 22 | 6.25 | 169 |
| 23 | 25 | 132 |
| 24 | 25 | 148 |
| 29 | 6.25 | 132 |
| 30 | 25 | 138 |
| 31 | 12.5 | 151 |

$$T/C\ (\%) = \frac{\text{Mean Survival Days of Test Samples}}{\text{Mean Survival Days of Control Samples}} \times 100$$

The experiment was carried out in the following manner. Lymphocytic leukemia P388 tumor cells ($1 \times 10^6$) were implanted intraperitoneally in CDF male mice (weight: about 22 g) divided into groups each consisting of five test mice. After 24 hours from the implantation, 0.2 ml of a phosphate-buffered aqueous physiological saline solution containing the active compound was intraperitoneally administered once to the test animals. The life-prolonging effect of the active compound was represented by T/C.

Compounds (I) and their pharmaceutically acceptable salts can be used as an antitumor agent or antitumor composition, singly or, in general, together with at least one pharmaceutically acceptable carrier. For instance, Compound (I) or its salt may be dissolved in a physiological saline solution or an aqueous solution of glucose, lactose, mannitol, etc. to obtain a pharmaceutical composition which is suitable as an injection. Compound (I) or its salt may also be freeze-dried in a conventional manner and sodium chloride is added thereto to obtain a powdery preparation for injection. The pharmaceutical compositions of the present invention thus prepared can optionally contain various additives which are well known in the field of pharmaceutics, such as pharmaceutically acceptable salts, etc., if desired. Although the amount of the composition for dosage varies in accordance with the age, condition, etc. of patients, it is suitable to administer the composition in an amount of 0.003 to 1 mg/kg/day as Compound (I) to mammals including human beings. The administration is effected, for example, once a day (by single administration or continuous administration), or one to three times a week intermittently, or once in two to three weeks, by intravenous injection. If desired, the composition can be orally administered in the same amount and in the same manner. The preparations for oral administration include tablets, capsules, powder, granules, ampules, etc., and these can contain various pharmaceutical carriers which are well known in the field of pharmaceutics. In addition, intra-arterial administration, intraperitoneal administration, intrathoracic administration, etc. are also possible, if desired, in the same amount of the composition and in the same manner as mentioned above.

The antitumor compositions of the present invention are expected to be effective against leukemia, stomach cancer, intestinal carcinoma, lung cancer, breast cancer, uterine carcinoma, etc. of mammals including human beings.

EXAMPLES

Structures and compound numbers of typical Compounds (I) are shown in Table 2.

TABLE 2

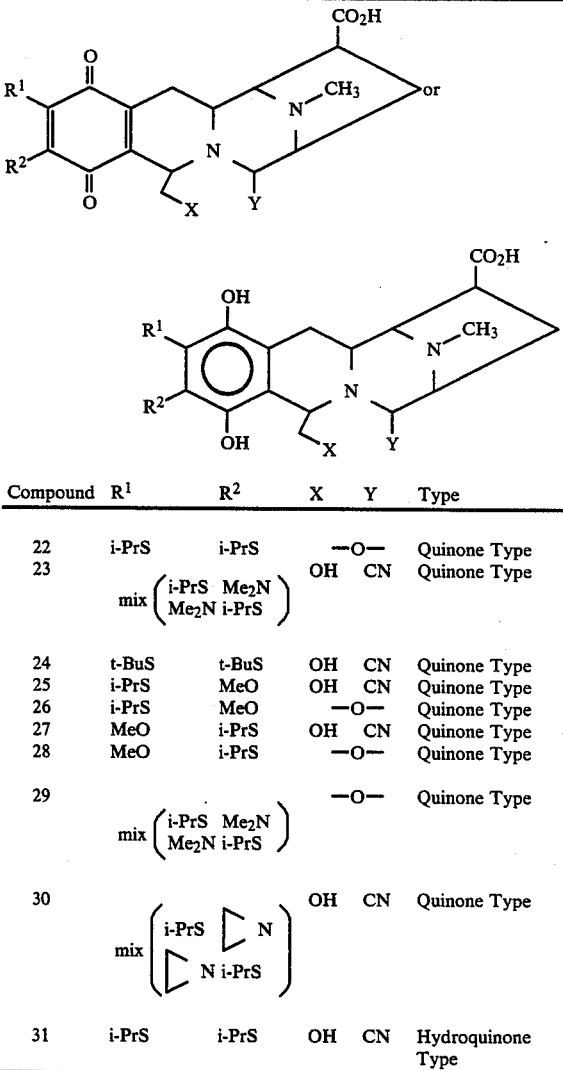

| Compound | $R^1$ | $R^2$ | X | Y | Type |
|---|---|---|---|---|---|
| 1 | H | H | OH | CN | Quinone Type |
| 2 | MeS | MeS | OH | CN | Quinone Type |
| 3 | MeS | MeS | —O— | | Quinone Type |
| 4 | EtS | EtS | OH | CN | Quinone Type |
| 5 | mix(MeS Me₂N / Me₂N MeS) | | OH | CN | Quinone Type |
| 6 | mix(EtS Me₂N / Me₂N EtS) | | OH | CN | Quinone Type |
| 7 | H | Me₂N | OH | CN | Quinone Type |
| 8 | Me₂N | H | OH | CN | Quinone Type |
| 9 | mix(PhS H / H PhS) | | OH | CN | Quinone Type |
| 10 | mix(H N₃ / N₃ H) | | OH | CN | Quinone Type |
| 11 | mix(MeO H / H MeO) | | OH | CN | Quinone Type |
| 12 | MeO | EtS | OH | CN | Quinone Type |
| 13 | EtS | MeO | OH | CN | Quinone Type |
| 14 | H | H | OH | CN | Hydroquinone Type |
| 15 | MeS | MeS | OH | CN | Hydroquinone Type |
| 16 | MeS | MeS | —O— | | Hydroquinone Type |
| 17 | EtS | EtS | OH | OH | Hydroquinone Type |
| 18 | EtS | EtS | —O— | | Quinone Type |
| 19 | n-PrS | n-PrS | OH | CN | Quinone Type |
| 20 | n-PrS | n-PrS | —O— | | Quinone Type |
| 21 | i-PrS | i-PrS | OH | CN | Quinone Type |
| 22 | i-PrS | i-PrS | —O— | | Quinone Type |
| 23 | mix(i-PrS Me₂N / Me₂N i-PrS) | | OH | CN | Quinone Type |
| 24 | t-BuS | t-BuS | OH | CN | Quinone Type |
| 25 | i-PrS | MeO | OH | CN | Quinone Type |
| 26 | i-PrS | MeO | —O— | | Quinone Type |
| 27 | MeO | i-PrS | OH | CN | Quinone Type |
| 28 | MeO | i-PrS | —O— | | Quinone Type |
| 29 | mix(i-PrS Me₂N / Me₂N i-PrS) | | —O— | | Quinone Type |
| 30 | mix(i-PrS [N / N i-PrS) | | OH | CN | Quinone Type |
| 31 | i-PrS | i-PrS | OH | CN | Hydroquinone Type |

The physico-chemical data shown hereinafter in the Examples and Reference Examples were measured with the following instruments.

IR: Nippon Bunko, IR-810
NMR: Varian, EM-390 (90 MHz); Nippon Denshi, FX-100 (100 MHz); Bruker, AM400 (400 MHz)
MS: Hitachi, B-80

EXAMPLE 1

Synthesis of Compound 1

Compound a obtained in Reference Example 1 (4 g) was dissolved in 40 ml of water, and 12 ml of 1N-sodium acetate was added thereto. A solution of 12.9 g of Fremy's salt in 400 ml of water was added dropwise thereto at room temperature. The resulting solution was stirred for 40 minutes at room temperature, and then hydrochloric acid was added thereto to adjust the pH thereof to 4.0. After concentration, the residue was purified by chromatography (Diaion HP-20, water:methanol=1:0 to 3:1) to obtain 2.08 g (53.2%) of Compound 1.

$^{13}$C NMR($D_2O$): 187.1, 187.0, 176.2, 141.8, 138.9, 137.8, 137.1, 115.9, 70.2, 65.8, 63.4, 57.3, 55.7, 54.8, 41.0, 40.4, 28.5, 24.2

$^1$H NMR (CD$_3$OD): 6.78(d, 1H, J=10.2 Hz), 6.75(d, 1H, J=10.2 Hz), 4.27(d, 1H, J=2.9 Hz), 3.82(m, 1H), 3.79(dd, 1H, J=11.4, 2.3 Hz), 3.61(dd, 1H, J=11.4, 3.7 Hz), 3.52(dd, 1H, J=6.4, 2.6 Hz), 3.51(bs, 1H), 3.22(dd, 1H, J=9.7, 5.9Hz), 2.78(m, 1H), 2.73(ddd, 1H, J=17.3, 2.9, 1.1 Hz), 2.59(dt, 1H), 2.33(s, 3H), 2.15(ddd, 1H, J=17.3, 10.9, 2.6 Hz), 2.02(dd, 1H, J=13.4, 9.7 Hz)

SIMS: 360 (M+3)$^+$

EXAMPLE 2

Synthesis of Compound 2

Compound 1 obtained in Example 1 (3.0 g) was dissolved in a mixed solvent comprising 80 ml of acetonitrile and 80 ml of 0.2M acetate buffer (pH 4.0). 4.5 ml of 15% aqueous solution of sodium methanethiolate was added thereto and the mixture was stirred at room temperature for one hour, followed by addition of 4.5 g of Fremy's salt and 140 ml of water. After stirring for 40 minutes, 20 ml of acetate buffer solution and 3.0 ml of aqueous sodium methanethiolate solution were added. After stirring for 50 minutes, 2.0 g of Fremy's salt and 50 ml of water were added. The mixture was stirred for 30 minutes, and 2.3 g of Fremy's salt was further added. After stirring for 30 minutes, the reaction mixture was concentrated under reduced pressure, whereby excess methylmercaptane and acetonitrile were evaporated. The residue was extracted twice with ethyl acetate, and the resulting extract was washed with a saturated sodium chloride solution and dried over anhydrous sodium sulfate. By concentration under reduced pressure, 3.56 g of a crude product was obtained. The product was then purified by chromatography (Wako-gel C-200, 450 ml; chloroform:methanol=1:0 to 20:1) to obtain 3.22 g (85.5%) of Compound 2.

$^1$H NMR (CDCl$_3$-CD$_3$OD): 4.05(d, 1H, J=2.7 Hz), 3.95(m, 1H), 3.79(dd, 1H, J=11.7, 2.8 Hz), 3.65(dd, 1H, J=11.7, 3.3 Hz), 3.53(bs, 1H), 3.52(m, 1H), 3.05(dd, 1H, J=9.6, 5.8 Hz), 2.91(bd, 1H, J=11.0 Hz), 2.81(ddd, 1H, J=18.0, 3.0, 1.2 Hz), 2.63(m, 1H), 2.63(s, 3H), 2.61(s, 3H), 2.36(s, 3H), 2.12(ddd, 1H, J=18.0, 11.0, 2.8 Hz), 1.95(dd, 1H, J=13.6, 9.7 Hz)

SIMS: 452 (M+3)$^+$ $^{13}$C NMR (CDCl$_3$-CD$_3$OD): 178.9, 178.8, 177.3, 145.4, 144.9, 142.6, 140.0, 116.9, 69.8, 64.6, 63.2, 58.1, 56.8, 56.1, 42.5, 41.8, 28.7, 25.4, 18.2, 18.1

EXAMPLE 3

Synthesis of Compound 3

Compound 2 obtained in Example 2 (1.0 g) was dissolved in 30 ml of acetonitrile. 560 mg of silver nitrate was added and the mixture was stirred at room temperature. After one hour, 300 mg of silver nitrate was further added and the mixture was stirred for 40 minutes, followed by addition of 10 ml of water. The insoluble substances were filtered off with Celite under reduced pressure, and the resulting filtrate was concentrated. The residue was purified by chromatography (Diaion HP-20, 100 ml; water:methanol=1:0 to 1:1) to obtain 769 mg (81.8%) of Compound 3.

$^1$H NMR (CD$_3$OD): 4.48(d, 1H, J=3.2 Hz), 4.22(m, 1H), 4.14(bd, 1H, J=8.0 Hz), 4.12(bs, 1H), 3.79(dd, 1H, J=11.5, 2.8 Hz), 3.56(dd, 1H, J=11.5, 3.9 Hz), 3.27-3.31(m, 2H), 2.83(dd, 1H, J=17.3, 2.3 Hz), 2.78(s, 3H), 2.62(m, 1H), 2.57(s, 3H), 2.55(s, 3H), 2.28(dd, 1H, J=14.0, 10.5 Hz), 2.18(ddd, 1H, J=17.2, 11.2, 2.2 Hz)

SIMS: 425 (M+3)$^+$ $^{13}$C NMR (CD$_3$OD): 180.7, 180.2, 146.8, 146.7, 143.8, 142.7, 90.9, 72.7, 66.5, 64.9, 56.2, 54.3, 43.1, 41.2, 28.5, 26.2, 18.5

EXAMPLE 4

Synthesis of Compound 15

Compound 2 obtained in Example 2 (500 mg) was dissolved in 20 ml of methanol. 150 mg of 5% Pd-C was added and the mixture was stirred in a stream of hydrogen at room temperature for one hour. The catalyst was filtered off with Celite under reduced pressure, and then the solvent was evaporated to obtain 486 mg (96.7%) of Compound 15.

$^1$H NMR (CDCl$_3$): 4.21(m, 1H), 4.10(d, 1H, J=2.6 Hz), 3.82(dd, 1H, J=11.1, 2.8 Hz), 3.70(dd, 1H, J=11.1, 3.5 Hz), 3.56(s, 1H), 3.51(m, 1H), 3.21(dd, 1H, J=9.3, 5.8 Hz), 2.98-3.02(m, 2H), 2.63(dt, 1H, J=13.2, 6.6 Hz), 2.35-2.40(m, 1H), 2.354(s, 6H), 2.347(s, 3H), 2.04(dd, 1H, J=13.2, 9.8 Hz)

SIMS: 452 (M+1)$^+$ $^{13}$C NMR (CDCl$_3$-CD$_3$OD): 178.2, 147.9, 147.2, 124.5, 123.0, 122.3, 122.0, 117.6, 70.1, 64.8, 64.4, 58.3, 57.7, 56.8, 42.5, 41.6, 28.6, 26.7, 19.7, 19.6

EXAMPLE 5

Synthesis of Compound 16

Compound 3 obtained in Example 3 (200 mg) was dissolved in 3 ml of methanol, and 2 ml of acetate buffer solution (pH 4.0) was added thereto. 60 mg of 10% Pd-C was added and the mixture was stirred in a stream of hydrogen at room temperature for one hour and 15 minutes. The catalyst was removed by filtration under reduced pressure, and the resulting filtrate was concentrated. The residue was purified by chromatography (Diaion HP-20, 20 ml; water:methanol=1:0 to 1:1) to obtain 160 mg (79.6%) of Compound 16.

$^1$H NMR (CD$_3$OD): 4.57(d, 1H, J=3.1 Hz), 4.53(dd, 1H, J=6.3, 3.0 Hz), 4.15(bs, 1H), 4.12(m, 1H), 3.75(dd, 1H, J=10.9, 3.0 Hz), 3.50(dd, 1H, J=10.9, 6.4 Hz), 3.39(dd, 1H, J=10.5, 5.1 Hz), 3.37(bd, 1H, J=12.3 Hz), 3.08(dd, 1H, J=15.4, 2.6 Hz), 2.80(s, 3H), 2.63(m, 1H), 2.46(dd, 1H, J=14.9, 10.6 Hz), 2.43(dd, 1H, J=15.2, 12.0 Hz), 2.33(s, 3H), 2.32(s, 3H)

SIMS: 425 (M+1)$^+$ $^{13}$C NMR (CD$_3$OD): 179.3, 149.6, 149.1, 125.9, 125.4, 124.9, 124.4, 92.1, 73.1, 67.3, 66.7, 56.7, 55.0, 42.8, 40.6, 28.2, 27.0, 20.0, 19.8

EXAMPLE 6

Synthesis of Compound 5

Compound 2 obtained in Example 2 (300 mg) was dissolved in 3 ml of acetonitrile. 3 ml of 1M dimethylamine hydrochloride solution and 1.5 ml of 1M potassium carbonate solution were added and the mixture was stirred at room temperature. After 4 hours, 1 ml of 1M dimethylamine hydrochloride solution and 0.5 ml of 1M potassium carbonate solution were added and the mixture was further stirred for 4 hours. After 5 ml of acetate buffer solution (pH 4.0) was added, acetonitrile was evaporated under reduced pressure, and the residue was extracted three times with ethyl acetate. The resulting extract was washed with saturated sodium chloride solution and dried over anhydrous sodium sulfate, and then the solvent was evaporated under reduced pressure to obtain 330 mg of a crude product. The product was purified by chromatography (Wako-gel C-200;

chloroform:methanol=1:0 to 50:1) to obtain 174.5 mg (58.6%) of Compound 5.

$^1$H NMR (CD$_3$OD): 4.25(m, 1H), 3.86(m, 1H), 3.79(dd, 0.4H, J=11.4, 2.3 Hz), 3.75(dd, 0.6H, J=11.7, 2.6 Hz), 3.61(dd, 0.6H, J=11.6, 3.6 Hz), 3.60(dd, 0.4H, J=11.5, 3.6 Hz), 3.52(dd, 1H, J=6.2, 2.3 Hz), 3.50(bs, 1H), 3.19(s, 2.4H), 3.18(s, 3.6H), 3.17-3.21(m, 1H), 2.65-2.80(m, 2H), 2.58(m, 1H), 2.32(s, 3H), 2.16(s, 1.8H), 2.15(s, 1.2H), 2.08-2.14(m, 1H), 2.02(dd, 0.4H, J=13.4, 9.6 Hz), 2.00(dd, 0.6H, J=13.3, 9.6 Hz)

SIMS: 449 (M+3)$^+$

EXAMPLE 7

Synthesis of Compound 4

Compound 1 obtained in Example 1 (1.0 g) was dissolved in 20 ml of water and 20 ml of acetonitrile. 0.42 ml of ethanethiol was added and the mixture was stirred at room temperature. After 40 minutes, 1.5 g of Fremy's salt and 40 ml of water were added and stirring was continued. After one hour, 1 g of Fremy's salt and 20 ml of water were added. After one hour, 400 mg of Fremy's salt was added and the mixture was further stirred for 30 minutes.

The ethanethiol and the acetonitrile were evaporated, and the residue was extracted four times with ethyl acetate. The resulting extract was washed with saturated sodium chloride solution and dried over anhydrous sodium sulfate, and then the solvent was evaporated under reduced pressure to obtain 1.17 g of a crude product. The product was purified by chromatography (Wako-gel C-200, 180 ml; chloroform:methanol=1:0 to 50:1) to obtain 1.14 g (85.3%) of Compound 4.

$^1$H NMR (CDCl$_3$-CD$_3$OD): 4.12(d, 1H, J=2.9 Hz), 3.94(m, 1H), 3.79(dd, 1H, J=11.6, 2.7 Hz), 3.61(dd, 1H, J=11.6, 3.8 Hz), 3.53(bs, 1H), 3.51(dd, 1H, J=6.3, 2.4H), 3.16-3.23(m, 4H), 3.08(dd, 1H, J=9.6, 5.8 Hz), 2.89(m, 1H), 2.82(m, 1H), 2.61(dt, 1H, J=13.3, 6.3Hz), 2.35(s, 3H), 2.13(ddd, 1H, J=17.8, 10.9, 2.9 Hz), 1.97(dd, 1H, J=13.5, 9.7 Hz), 1.302(t, 3H, J=7.4 Hz), 1.296(t, 3H, J=7.4 Hz).

SIMS: 480 (M+3)$^+$ $^{13}$C NMR (CDCl$_3$-CD$_3$OD): 179.2, 179.1, 177.5, 145.4, 145.0, 142.6, 140.2, 117.1, 69.9, 64.7, 63.5, 58.2, 57.0, 56.3, 42.6, 41.8, 29.23, 29.15, 28.6, 25.5, 15.3

EXAMPLE 8

Synthesis of Compound 17

Compound 4 obtained in Example 7 (500 mg) was dissolved in 20 ml of methanol, and 150 mg of 5% Pd-C was added thereto. The mixture was stirred in a stream of hydrogen at room temperature for one hour. The catalyst was filtered off, and the solvent was evaporated under reduced pressure to obtain 460 mg of a crude product. The product was purified by chromatography (Wako-gel C-200, 50 ml; chloroform:methanol=1:0 to 50:1) to obtain 396 mg (78.8%) of Compound 17.

$^1$H NMR (CDCl$_3$): 4.23(m, 1H), 4.06(bs, 1H), 3.82(dd, 1H, J=11.1, 3.1 Hz), 3.75(dd, 1H, J=11.1, 4.0 Hz), 3.58(bs, 1H), 3.54(m, 1H), 3.24(dd, 1H, J=9.3, 5.7 Hz), 3.06(m, 1H), 3.01(m, 1H), 2.82(q, 2H, J=7.4 Hz), 2.81(q, 2H, J=7.4 Hz), 2.65(dt, 1H, J=13.7, 6.5 Hz), 2.39(s, 3H), 2.37(m, 1H), 2.04(dd, 1H, J=13.7, 9.3 Hz), 1.214(t, 3H, J=7.4 Hz), 1.210(t, 3H, J=7.4 Hz)

SIMS: 480 (M+1)$^+$ $^{13}$C NMR (CDCl$_3$): 179.8, 148.7, 147.9, 124.1, 122.8, 120.9, 120.7, 117.5, 70.3, 64.8, 64.5, 58.5, 57.5, 56.7, 42.7, 41.7, 31.0, 30.9, 28.8, 26.9, 14.9, 14.8

EXAMPLE 9

Synthesis of Compound 6

Compound 4 obtained in Example 7 (50 mg) was dissolved in 1 ml of acetonitrile and 1 ml of water. 0.5 ml of 1M dimethylamine hydrochloride solution and 0.25 ml of 1M potassium carbonate solution were added thereto and the mixture was stirred at room temperature. After 4 hours and 30 minutes, 0.15 ml of 1M dimethylamine hydrochloride solution and 75 μl of 1M potassium carbonate solution were further added and stirring was continued. After 5 hours, 0.2 ml of 1M dimethylamine hydrochloride solution and 0.1 ml of 1M potassium carbonate solution were added and the mixture was further stirred for 2 hours. Then, 3 ml of acetate buffer solution (pH 4.0) was added, and the acetonitrile was evaporated under reduced pressure. The reaction mixture was extracted with ethyl acetate, washed with saturated sodium chloride solution and dried over anhydrous sodium sulfate, followed by evaporation of the solvent. The crude product thus obtained was purified by chromatography (Wako-gel C-200, 10 ml; chloroform:methanol=1:0 to 50:1) to obtain 24.3 mg (50.4%) of Compound 6.

$^1$H NMR (CDCl$_3$): 4.03(d, 0.4H, J=2.6 Hz), 4.00(d, 0.6H, J=2.5 Hz), 3.96(m, 0.4H), 3.94(m, 0.6H), 3.80(m, 1H), 3.69(m, 1H), 3.53(bs, 2H), 3.18(s, 6H), 3.11(dd, 1H, J=9.4, 5.9 Hz), 2.78-2.94(m, 2H), 2.60-2.71(m, 3H), 2.36(s, 3H), 2.04-2.19(m, 1H), 1.95(dd, 1H, J=13.2, 9.8 Hz), 1.20(t, 1.2H, J=7 Hz), 1.19(t, 1.8H, J=7.4 Hz)

SIMS: 463 (M+3)$^+$

EXAMPLE 10

Synthesis of Compounds 7 and 8

In this example, 457 mg of dimethylamine hydrochloride, 232 mg of potassium carbonate and 224 mg of copper acetate were dissolved in 13 ml of methanol. To the resulting solution was added dropwise a solution of 400 mg of Compound 1 obtained in Example 1 in 26 ml of methanol at room temperature. The resulting solution was stirred in an atmosphere of oxygen at room temperature for 40 minutes. 20 ml of acetate buffer solution (pH 4.0) was added, and the methanol was evaporated under reduced pressure. The residue was purified by chromatography (Diaion HP-20, 70 ml; water:methanol=1:0 to 1:1), whereby 344 mg of a crude product was obtained.

The product was subjected to HPLC (Nucleosil 10 C$_{18}$, φ20×250, 10% acetonitrile-0.01M ammonium acetate) to obtain 170 mg (38%) of Compound 7 and 131 mg (29%) of Compound 8.

Compound 7:

$^1$H NMR (D$_2$O): 5.55(s, 0.7H), 4.60(d, 1H, J=2.5 Hz), 4.15(m, 1H), 4.03(bs, 1H), 3.96(m, 1H), 3.80(dd, 1H, J=12.1, 2.4 Hz), 3.65(dd, 1H, J=12.1, 3.6 Hz), 3.20-3.28(m, 1H), 3.17(s, 6H), 3.06(bd, 1H, J=9.3 Hz), 2.80(m, 1H), 2.64-2.70(m, 1H), 2.64(s, 3H), 2.28(m, 1H), 2.20(m, 1H)

SIMS: 403 (M+3)$^+$ $^{13}$C NMR (D$_2$O): 184.3, 183.7, 153.7, 143.8, 136.6, 117.4, 101.1, 70.8, 65.6, 62.7, 57.7, 56.6, 55.7, 43.3, 43.3, 41.3, 29.6, 25.2

Compound 8:

$^1$H NMR (D$_2$O): 5.51(s, 0.7H), 4.55(d, 1H, J=2.7 Hz), 4.08(m, 1H), 3.96(bs, 1H), 3.89(m, 1H), 3.85(dd, 1H, J=11.8, 2.4 Hz), 3.67(dd, 1H, J=11.8, 3.4 Hz), 3.18-3.23(m, 1H), 3.17(s, 6H), 3.00(bd, 1H, J=9.0 Hz), 2.79(m, 1H), 2.65(m, 1H), 2.58(s, 3H), 2.24(dd, 1H, J=14.1, 10.4 Hz), 2.17(ddd, 1H, J=17.2, 10.8, 2.3 Hz)

SIMS: 403 (M+3)$^+$ $^{13}$C NMR (D$_2$O): 184.4, 184.2, 153.2, 140.1, 139.5, 117.6, 101.5, 70.8, 65.6, 63.4, 58.1, 56.7, 56.0, 43.2, 43.2, 41.4, 29.6, 25.1

EXAMPLE 11

Synthesis of Compound 9

Compound 1 obtained in Example 1 (200 mg) was dissolved in 20 ml of methanol, and 46 μl of thiophenol was added thereto. The mixture was stirred at room temperature for one hour, and 10 ml of water and 300 mg of Fremy's salt were added. After the mixture was stirred for one hour and 50 minutes, 15 ml of acetate buffer solution (pH 4.0) was added, and the methanol was evaporated under reduced pressure. The residue was extracted three times with ethyl acetate, washed with saturated sodium chloride solution and dried over anhydrous sodium sulfate. Then, the solvent was evaporated to obtain 220 mg of a crude product. The product was purified by chromatography (Wako-gel C-200, 40 ml; chloroform:methanol=100:1) to obtain 121.5 mg (46.6%) of Compound 9.

$^1$H NMR (CD$_3$OD-D$_2$O): 7.55–7.61(m, 5H), 5.79(s, 0.9H), 5.75(s, 0.1H), 4.36(d, 1H, J=2.8 Hz), 3.88(m, 1H), 3.86(dd, 1H, J=11.6, 2.2 Hz), 3.68(dd, 1H, J=11.6, 3.4 Hz), 3.67(m, 1H), 3.63(bs, 1H), 3.11(dd, 1H, J;32 9.7, 5.6 Hz), 2.82(bd, 1H, J=10.1 Hz), 2.74(dd, 1H, J=17.9, 2.3 Hz), 2.60(dt, 1H, J=13.1, 6.3 Hz), 2.36(s, 3H), 2.16(dd, 1H, J=17.9, 11.0 Hz), 2.09(dd, 1H, J=13.5, 10.0 Hz)

SIMS: 468 (M+3)$^+$ $^{13}$C NMR (CD$_3$OD-D$_2$O): 184.1, 183.9, 181.9, 179.3, 156.3, 145.0, 139.8, 136.8, 132.1, 131.8, 128.2, 126.6, 118.8, 71.0, 65.9, 63.6, 59.0, 58.1, 57.3, 44.9, 42.4, 30.3, 26.3

EXAMPLE 12

Synthesis of Compound 10

Compound d obtained in Reference Example 4 (250 mg) was dissolved in 10 ml of methylene chloride, and 0.5 ml of anisole and 1 ml of trifluoroacetic acid were added thereto. After being stirred at room temperature for 2 hours, the reaction mixture was concentrated and purified by chromatography (Diaion HP-20, 30 ml; water:methanol=1:0 to 3:7) to obtain 114 mg (64.5%) of Compound 10.

$^1$H NMR (D$_2$O): 6.57(bs, 0.3H), 6.39(bs, 0.7H), 4.41(m, 1H), 4.28(bs, 1H), 4.00(m, 1H), 3.87(dd, 1H, J=12.0, 2.3 Hz), 3.68(dd, 1H, J=12.1, 3.9 Hz), 3.41(dd, 1H, J=10.5, 5.6 Hz), 3.18(bd, 1H, J=8.7 Hz), 2.81–2.93(m, 1H), 2.83(s, 3H), 2.75(m, 1H), 2.43(dd, 1H, J=14.5, 10.7 Hz)

SIMS: 401 (M+3)$^+$

EXAMPLE 13

Synthesis of Compound 11

Compound e obtained in Reference Example 5 (300 mg) was dissolved in 15 ml of methylene chloride, and 0.8 ml of anisole and 1.2 ml of trifluoroacetic acid were added thereto. After being stirred at room temperature for one hour and 40 minutes, the reaction mixture was concentrated and purified by chromatography (Diaion HP-20, 40 ml; water:methanol=1:0 to 1:1) to obtain 147 mg (70.0%) of Compound 11.

$^1$H NMR (D$_2$O): 6.02(s, 0.6H), 5.99(s, 0.4H), 4.73(d, 1H, J=2.9 Hz), 4.36(m, 1H), 4.23(bs, 1H), 3.94(m, 1H), 3.82(m, 1H), 3.80(s, 3H), 3.63(dd, 1H, J=12.1, 3.8 Hz), 3.36(dd, 1H, J=10.4, 5.5 Hz), 3.14(bd, 1H, J;32 10.7 Hz), 2.86(m, 1H), 2.79(s, 3H), 2.72(m, 1H), 2.38(dd, 1H, J=14.4, 10.6 Hz), 2.24(m, 1H)

SIMS: 390 (M+3)$^+$

EXAMPLE 14

Synthesis of Compound 12

Compound f obtained in Reference Example 6 (220 mg) was dissolved in 6 ml of methylene chloride, and 0.2 ml of anisole and 0.6 ml of trifluoroacetic acid were added thereto. After being stirred at room temperature for one hour, the reaction mixture was concentrated and purified by chromatography (Diaion HP-20, 20 ml; water:methanol=1:0 to 1:2) to obtain 143 mg (88.8%) of Compound 12.

$^1$H NMR (D$_2$O): 4.41(bd, 1H, J=6.6 Hz), 4.28(bs, 1H), 4.09(s, 3H), 4.02(m, 1H), 3.86(dd, 1H, J=12.0, 2.5 Hz), 3.40(dd, 1H, J=10.5, 5.5 Hz), 3.17(m, 1H), 2.98(m, 2H), 2.93(m, 1H), 2.83(s, 3H), 2.75(m, 1H), 2.42(dd, 1H, J=14.5, 10.5 Hz), 2.30 (ddd, 1H, J=17.5, 10.7, 2.4 Hz), 1.21(t, 3H, J=7.4 Hz)

SIMS: 450 (M+3)$^+$ $^{13}$C NMR (D$_2$O): 184.6, 180.6, 179.5, 159.1, 141.1, 139.7, 129.5, 116.4, 71.9, 66.0, 63.4, 62.2, 57.9, 56.0, 55.1, 42.6, 41.1, 29.3, 28.4, 24.5, 15.2

EXAMPLE 15

Synthesis of Compound 13

Compound g obtained in Reference Example 6 (358 mg) was dissolved in 10 ml of methylene chloride, and 0.3 ml of anisole and 1 ml of trifluoroacetic acid were added thereto. After being stirred at room temperature for one hour and 10 minutes, the reaction mixture was concentrated and purified by chromatography (Diaion HP-20, 50 ml; water; methanol=1:0 to 1:2) to obtain 200 mg (77.0%) of Compound 13.

$^1$H NMR (CD$_3$OD): 4.55(d, 1H, J=2.7 Hz), 4.03(s, 3H), 3.96(m, 1H), 3.91(bs, 1H), 3.83(dd, 1H, J=11.6, 2.3 Hz), 3.64(dd, 1H, J=11.6, 4.1 Hz), 3.43(dd, 1H, J=10.0, 5.7 Hz), 3.07(q, 2H, J=7.4 Hz), 2.97(m, 1H), 2.84(dd, 1H, J=17.5, 2.1 Hz), 2.71(m, 1H), 2.61(s, 3H), 2.24(dd, 1H, J=13.8, 10.2 Hz), 2.20(ddd, 1H, J=17.6, 10.9, 2.5 Hz), 1.25(t, 3H, J=7.4 Hz)

SIMS: 450 (M+3)$^+$ $^{13}$C NMR (CD$_3$OD): 184.1, 180.4, 177.0, 158.1, 142.9, 138.6, 130.9, 117.2, 71.3, 66.3, 64.1, 61.6, 58.7, 57.3, 56.6, 42.2, 41.7, 29.2, 28.0, 25.9, 15.6

EXAMPLE 16

Synthesis of Compound 14

Compound 1 obtained in Example 1 (300 mg) was dissolved in 20 ml of acetate buffer solution (pH 4.0), and 100 mg of 10% Pd-C was added thereto. The mixture was stirred in an atmosphere of hydrogen for 3 hours and 30 minutes. The catalyst was removed by filtration, and the resulting filtrate was concentrated and purified by chromatography (Diaion HP-20, 40 ml; only water) to obtain 89 mg (29.2%) of Compound 14.

SIMS: 360 (M+1)$^+$ $^1$H NMR (CD$_3$OD): 6.53(s, 2H), 4.27(d, 1H), 4.17(m, 1H), 3.52(bs, 1H), 3.3–3.9(m, 3H), 3.13(m, 1H), 2.4–3.0(m, 4H), 2.35(s, 3H), 2.12(m, 1H)

EXAMPLE 17

Synthesis of Compound 18

Compound 4 obtained in Example 7 (300 mg) was dissolved in 6 ml of acetonitrile and 3 ml of methanol. 267 mg of silver nitrate was added, and the resulting mixture was stirred at room temperature for three hours, followed by addition of 6 ml of 1N-HCl. The insoluble substances were filtered off with Celite under reduced pressure, and the filtrate was concentrated. The residue was purified by chromatography (Diaion HP-20, 40 ml; water:methanol=1:0 to 3:7) to obtain 218 mg (77.0%) of Compound 18.

$^1$H NMR (CD$_3$OD): 4.48(d, 1H, J=3.2 Hz), 4.23 (m, 1H), 4.13(m, 1H), 4.11(bs, 1H), 3.80(dd, 1H, J=11.5, 2.8 Hz), 3.56(dd, 1H, J=11.5, 3.9 Hz), 3.05–3.21(m, 4H), 2.85(dd, 1H, J=17.2, 2.3 Hz), 2.78(s, 3H), 2.61(m, 1H), 2.28(dd, 1H, J=14.0, 10.5 Hz), 2.19(ddd, 1H, J=17.1, 11.1, 2.4 Hz), 1.25(t, 6H, J=7.4 Hz)

SIMS: 453 (M+3)+

EXAMPLE 18

Synthesis of Compound 19

Compound 1 obtained in Example 1 (500 mg) was dissolved in 5 ml of acetonitrile and 10 ml of water, and 0.19 ml of n-propanethiol was added. The resulting mixture was stirred at room temperature for one hour, and 750 mg of Fremy's salt was added. After 30 minutes, 0.19 ml of n-propanethiol was added, and stirring was continued for 30 minutes. Then, 750 mg of Fremy's salt, 10 ml of water and 5 ml of acetonitrile were added, and the mixture was stirred for one hour. 200 mg of Fremy's salt was added, and after 30 minutes, 750 mg of Fremy's salt was further added, followed by stirring for 50 minutes. Excess n-propanethiol and acetonitrile were evaporated under reduced pressure, and acetate buffer (pH 4.0) was added to the residue. The mixture was extracted twice with ethyl acetate, and the combined extracts were washed with saturated sodium chloride solution, dried over anhydrous sodium sulfate, and concentrated under reduced pressure, whereby 710 mg of a crude product was obtained. The product was purified by chromatography (Wako-gel C-200, 60 ml; chloroform:methanol=1:0 to 50:1) to obtain 509 mg (71.9%) of Compound 19.

$^1$H NMR (CD$_3$OD): 4.16(d, 1H, J=2.9 Hz), 3.78(m, 1H), 3.68(dd, 1H, J=11.4, 2.6 Hz), 3.51(dd, 1H, J=11.4, 3.7 Hz), 3.43(m, 1H), 3.40(bs, 1H), 2.91–3.20(m, 5H), 2.66–2.70(m, 2H), 2.50(m, 1H), 2.23(s, 3H), 2.05(ddd, 1H, J=18.0, 11.4, 2.9 Hz), 1.91(dd, 1H, J=13.2, 9.5 Hz), 1.51(m, 4H), 0.912(t, 3H, J=7.3 Hz), 0.907(t, 3H, J=7.3 Hz)

SIMS: 508 (M+3)+

EXAMPLE 19 CL Synthesis of Compound 20

Compound 19 obtained in Example 18 (300 mg) was dissolved in 6 ml of acetonitrile and 3 ml of methanol. Silver nitrate (252 mg) was added, and the resulting mixture was stirred at room temperature for two hours and fifty minutes. Silver nitrate (80 mg) was further added, and the mixture was stirred at room temperature for an additional 50 minutes, followed by addition of 1N-HCl. The insoluble substances were filtered off with Celite under reduced pressure, and the filtrate was concentrated. The residue was purified by chromatography (Diaion HP-20, 40 ml; water:methanol=1:0 to 3:7) to obtain 228 mg (80.2%) of Compound 20.

$^1$H NMR (CD$_3$OD): 4.48(d, 1H, J=3.2 Hz), 4.23(m, 1H), 4.14(m, 1H), 4.11(bs, 1H), 3.79(dd, 1H, J=11.5, 2.8 Hz), 3.55(dd, 1H, J=11.5, 3.9 Hz), 2.99–3.20(m, 4H), 2.85(dd, 1H, J=17.3, 2.3 Hz), 2.78(s, 3H), 2.62(m, 1H), 2.28(dd, 1H, J=14.0, 10.5 Hz), 2.18(ddd, 1H, J=17.2, 11.1, 2.4 Hz), 1.60(m, 4H), 1.997(t, 3H, J=7.4 Hz), 1.996(t, 3H, J=7.4 Hz)

SIMS: 481 (M+3)+

EXAMPLE 20

Synthesis of Compound 21

Compound 1 obtained in Example 1 (500 mg) was dissolved in 5 ml of acetonitrile and 10 ml of water, and 0.26 ml of i-propanethiol was added. The resulting mixture was stirred at room temperature for one hour, and 1.07 g of Fremy's salt was added. After stirring for 15 minutes, 0.13 ml of i-propanethiol was added. After 45 minutes, 1.07 g of Fremy's salt and 10 ml of water were added, and the mixture was stirred for 1.5 hours. Then, 3 ml of water and 300 mg of Fremy's salt were added, and stirring was continued for 30 minutes. Excess i-propanethiol and acetonitrile were evaporated under reduced pressure, and acetate buffer (pH 4.0) was added to the residue. The mixture was extracted twice with ethyl acetate, and the combined extracts were washed with saturated sodium chloride solution and dried over anhydrous sodium sulfate. Then, the solvent was evaporated to obtain 580 mg of a crude product. The product was purified by chromatography (Wako-gel C-200, 60 ml; chloroform: methanol=1:0 to 50:1) to obtain 518 mg (73.2%) of Compound 21.

$^1$H NMR (CD$_3$OD): 4.26(d, 1H, J=2.9 Hz), 4.01–4.11(m, 2H), 3.89(m, 1H), 3.79(dd, 1H, J=11.5, 2.4 Hz), 3.62(dd, 1H, J=11.5, 3.7 Hz), 3.53(m, 1H), 3.51(bs, 1H), 3.22(dd, 1H, J=9.7, 5.7 Hz), 2.77–2.82(m, 2H), 2.60(m, 1H), 2.33(s, 3H), 2.17(ddd, 1H, J=18.0, 11.3, 2.8 Hz), 2.02(dd, 1H, J=13.4, 9.7 Hz), 1.23–1.30(m, 12H)

SIMS: 508 (M+3)+

EXAMPLE 21

Synthesis of Compound 22

Compound 21 obtained in Example 20 (300 mg) was dissolved in 6 ml of acetonitrile and 3 ml of methanol. Silver nitrate (250 mg) was added, and the resulting mixture was stirred at room temperature for one hour and twenty minutes. Silver nitrate (80 mg) was further added, and the mixture was stirred at room temperature for an additional two hours and fifty minutes, followed by addition of 1N—HCl. The insoluble substances were filtered off with Celite under reduced pressure, and the filtrate was concentrated. The residue was purified by chromatography (Diaion HP-20; water:methanol=1:0 to 3:7) to obtain 238 mg (83.8%) of Compound 22.

$^1$H NMR (CD$_3$OD): 4.49(d, 1H, J=3.2 Hz), 4.25(m, 1H), 4.13(m, 1H), 4.12(bs, 1H), 4.00–4.11(m, 2H), 3.81(dd, 1H, J=11.4, 2.8 Hz), 3.57(dd, 1H, J=11.4, 3.9 Hz), 2.87(dd, 1H, J=17.3, 2.2 Hz), 2.78(s, 3H), 2.62(m, 1H), 2.29(dd, 1H, J=14.1, 10.5 Hz), 2.21 (ddd, 1H, J=17.3, 11.1, 2.5 Hz), 1.23–1.29(m, 2H)

SIMS: 481 (M+3)+

EXAMPLE 22

Synthesis of Compound 23

Compound 21 obtained in Example 20 (1.11 g) was dissolved in 18 ml of acetonitrile. 20 ml of 1M aqueous solution of dimethylamine hydrochloride and 10 ml of 1M aqueous solution of potassium carbonate were added, and the mixture was stirred at room temperature. After 3.5 hours, 4 ml of 1M dimethylamine hydrochloride solution and 2 ml of 1M potassium carbonate solution were added, and stirring was continued at room temperature for 19 hours. After addition of acetate buffer (pH 4), the resulting mixture was concentrated and purified by chromatography (Diaion HP-20, 150 ml; water:methanol=1:0 to 1:2) to obtain 302 mg (29%) of Compound 23.

SIMS: 477 (M+3)+

EXAMPLE 23

Synthesis of Compound 24

Compound 1 obtained in Example 1 (600 mg) was dissolved in 15 ml of acetonitrile and 30 ml of water. 0.28 ml of t-butylmercaptan was added, and the resulting mixture was stirred at room temperature for 30 minutes, followed by addition of 1.29 g of Fremy's salt. After stirring for 50 minutes, 10 ml of acetonitrile and 0.28 ml of t-butylmercaptan were added, and stirring was continued for 35 minutes. Then, 1.29 g of Fremy's salt, 20 ml of water and 10 ml of acetonitrile were added, and the mixture was stirred for 35 minutes, followed by addition of 300 mg of Fremy's salt and 10 ml of water. After stirring for an additional one hour, excess t-butylmercaptan and acetonitrile were evaporated under reduced pressure, and the residue was extracted twice with ethyl acetate. The combined extracts were washed with saturated sodium chloride solution and dried over anhydrous sodium sulfate. Then, the solvent was evaporated to obtain 680 mg of a crude product. The product was purified by chromatography (Wako-gel C-200, 60 ml; chloroform:methanol=1:0 to 50:1) to obtain 475 mg (53.0%) of Compound 24.

$^1$H NMR (CDCl$_3$—CD$_3$OD): 4.27(d, 1H, J=2.4 Hz), 3.92(m, 1H), 3.54–3.90(m, 2H), 3.53(m, 2H), 3.23(dd, 1H, J=9.5, 5.6 Hz), 2.75–2.97(m, 2H), 2.59(m, 1H), 2.35(s, 3H), 1.91–2.27(m, 2H), 1.416(s, 9H), 1.411(s, 9H)

SIMS: 535 (M+3)+

EXAMPLE 24

Synthesis of Compound 25

Compound i obtained in Reference Example 7 (625 mg) was dissolved in 18 ml of methylene chloride, and 1 ml of anisole and 1.8 ml of trifluoroacetic acid were added. The resulting mixture was stirred at room temperature for two hours and twenty minutes. The reaction mixture was concentrated and purified by chromatography (Diaion HP-20, 70 ml; water:methanol=1:0 to 3:7) to obtain 400 mg (87.0%) of Compound 25.

$^1$H NMR (CD$_3$OD): 4.25(d, 1H, J=2.9 Hz), 4.04(s, 3H), 3.85(m, 1H), 3.83(m, 1H), 3.79(dd, 1H, J=11.5, 2.3 Hz), 3.64(dd, 1H, J=11.6, 3.6 Hz), 3.52(dd, 1H, J=6.4, 2.5 Hz), 3.49(bs, 1H), 3.20(dd, 1H, J=9.7, 5.7 Hz), 2.73–2.78(m, 2H), 2.59(m, 1H), 2.32(s, 3H), 2.14(ddd, 1H, J=18.0, 11.3, 2.8 Hz), 2.01(dd, 1H, J=13.4, 9.7 Hz), 1.24(d, 6H, J=6.7 Hz)

SIMS: 464 (M+3)+

EXAMPLE 25

Synthesis of Compound 26

Compound 25 obtained in Example 24 (129 mg) was dissolved in 3 ml of acetonitrile and 2 ml of water. 119 mg of silver nitrate was added, and the resulting mixture was stirred at room temperatur for four hours. The insoluble substances were filtered off with Celite under reduced pressure, and the filtrate was concentrated. The residue was purified by chromatography (Diaion HP-20, 10 ml; water:methanol=1:0 to 1:1) to obtain 99.6 mg (82.0%) of Compound 26.

$^1$H NMR (CD$_3$OD): 4.48(d, 1H, J=3.2 Hz), 4.20(m, 1H), 4.14(m, 1H), 4.11(bs, 1H), 4.04(s, 3H), 3.88 (m, 1H), 3.82(dd, 1H, J=11.5, 2.7 Hz), 3.59(dd, 1H, J=11.5, 3.8 Hz), 3.27(m, 1H), 2.84(dd, 1H, J=17.2, 2.3 Hz), 2.78(s, 3H), 2.62(m, 1H), 2.29(dd, 1H, J=14.1, 10.5 Hz), 2.19(ddd, 1H, J=17.2, 11.1, 2.6 Hz), 1.246(d, 3H, J=6.7 Hz), 1.244(d, 3H, J=6.7 Hz)

SIMS: 437 (M+3)+

EXAMPLE 26

Synthesis of Compound 27

Compound h obtained in Reference Example 7 (423 mg) was dissolved in 12 ml of methylene chloride, and 0.6 ml of anisole and 1.2 ml of trifluoroacetic acid were added. The resulting mixture was stirred at room temperature for 1.5 hours. The reaction mixture was concentrated and purified by chromatography (Diaion HP-20, 50 ml; water:methanol=1:0 to 3:7) to obtain 239 mg (76.9%) of Compound 27.

$^1$H NMR (CD$_3$OD): 4.25(d, 1H, J=2.9 Hz), 4.05(s, 3H), 3.86(m, 1H), 3.85(m, 1H), 3.78(dd, 1H, J=11.5, 2.3 Hz), 3.59(dd, 1H, J=11.5, 3.8 Hz), 3.52(dd, 1H, J=6.2, 2.4 Hz), 3.50(bs, 1H), 3.20(dd, 1H, J=9.7, 5.7 Hz), 2.71–2.79(m, 2H), 2.59(m, 1H), 2.32(s, 3H), 2.13(ddd, 1H, J=16.7, 10.1, 2.7 Hz), 2.01(dd, 1H, J=13.4, 9.7 Hz), 1.25(d, 3H, J=6.7 Hz), 1.22(d, 3H, J=6.72 Hz)

SIMS: 464 (M+3)+

EXAMPLE 27

Synthesis of Compound 28

Compound 27 obtained in Example 26 (110 mg) was dissolved in 2.5 ml of acetonitrile and 1.5 ml of water. 102 mg of silver nitrate was added, and the resulting mixture was stirred at room temperature for four hours. The insoluble substances were filtered off, and the filtrate was concentrated. The residue was purified by chromatography (Diaion HP-20, 10 ml; water:methanol=1:0 to 1:1) to obtain 88.4 mg (85.4%) of Compound 28.

$^1$H NMR (CD$_3$OD): 4.49(d, 1H, J=3.3 Hz), 4.21(m, 1H), 4.14(m, 1H), 4.11(bs, 1H), 4.06(s, 3H), 3.84(m, 1H), 3.80(dd, 1H, J=11.5, 2.6 Hz), 3.53(dd, 1H, J=11.5, 3.9 Hz), 3.27(m, 1H), 2.82(dd, 1H, J=17.1, 2.4 Hz), 2.78(s, 3H), 2.62(m, 1H), 2.30(dd, 1H, J=14.1, 10.5 Hz), 2.18(ddd, 1H, J=17.1, 11.1, 2.5 Hz), 1.25(d, 3H, J=6.7 Hz), 1.23(d, 3H, J=6.6 Hz)

SIMS: 437 (M+3)+

EXAMPLE 28

Synthesis of Compound 29

Compound 23 obtained in Example 22 (240 mg) was dissolved in 8 ml of acetonitrile and 2 ml of methanol. 217 mg of silver nitrate was added, and the resulting mixture was stirred at room temperature for one hour. After addition of water, the insoluble substances were filtered off, and the filtrate was concentrated. The residue was purified by chromatography (Diaion HP-20, 40 ml; water:methanol=1:0 to 1:1) to obtain 147 mg (64.9%) of Compound 29.

SIMS: 450 (M+3)+

EXAMPLE 29

Synthesis of Compound 30

Compound 21 obtained in Example 20 (90 mg) was dissolved in 1 ml of acetonitrile, and 2 ml of phosphate buffer (pH 7.7) was added. Then, 0.3 ml of an aqueous solution of ethyleneimine was added, and the resulting mixture was stirred at room temperature for one hour and forty minutes. The reaction mixture was concentrated and purified by chromatography (Diaion HP-20, 15 ml; water:methanol=1:0 to 3:2) to obtain 57 mg (67.8%) of Compound 30.

$^1$H NMR (CD$_3$OD): 4.24(m, 1H), 3.87(m, 0.4H), 3.81(m, 0.6H), 3.78(m, 1H), 3.69(m, 1H), 3.63(dd, 0.6H, J=11.4, 3.6 Hz), 3.57(dd, 0.4H, J=11.4, 3.9 Hz), 3.50(bs, 1H), 3.49(m, 1H), 3.12(m, 1H), 2.73-2.81(m, 2H), 2.58(m, 1H), 2.43-2.47(m, 4H), 2.32(s, 3H), 2.13(m, 1H), 1.99(m, 1H), 1.20-1.25(m, 6H)

SIMS: 475 (M+3)+

EXAMPLE 30

Synthesis of Compound 31

Compound 21 obtained in Example 20 (223 mg) was dissolved in 8 ml of methanol. 60 mg of 5% PD-C was added, and the mixture was stirred in an atmosphere of hydrogen at room temperature for 15 minutes. Afrer removal of the catalyst by filtration, the filtrate was concentrated to obtain 225 mg (quantitative) of Compound 31.

$^1$H NMR (CD$_3$OD): 4.33(d, 1H, J=2.6 Hz), 4.19(dd, 1H, J=6.0, 2.6 Hz), 3.84(dd, 1H, J=10.8, 2.6 Hz), 3.55(dd, 1H, J=10.8, 6.0 Hz), 3.52(bs, 1H), 3.51(m, 1H), 3.28-3.38(m, 3H), 3.00(dd, 1H, J=15.7, 2.5 Hz), 2.86(bd, 1H, J=11.0 Hz), 2.61(m, 1H), 2.40(dd, 1H, J=15.8, 11.7 Hz), 2.34(s, 3H), 2.13(dd, 1H, J=13.2, 9.8 Hz), 1.19-1.22(m, 12H)

SIMS: 508 (M+1)+

Structures and compound numbers of the compounds obtained in the following Reference Examples are shown below. In the following structural formulae, the moiety of

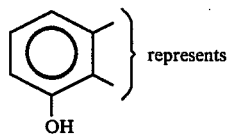 represents

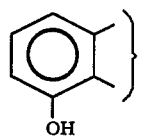 b

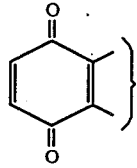 c

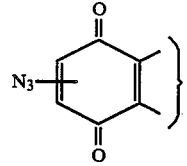 d

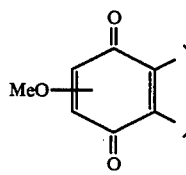 e

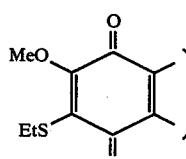 f

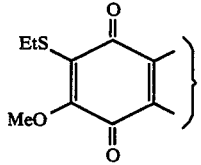 g

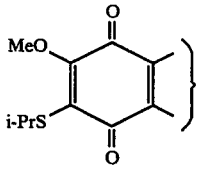 h

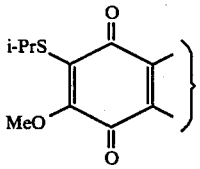 i

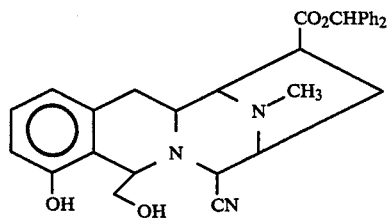 a

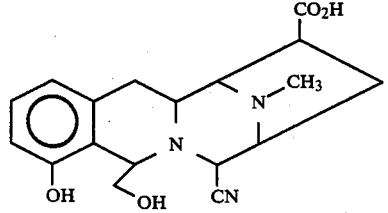

REFERENCE EXAMPLE 1

Synthesis of Compound a

DX-52-1 (15 g) was suspended in 150 ml of methylene chloride. Under cooling at −78° C., 150 ml of methylene chloride solution of boron tribromide (50 g/200 ml) was added dropwise to the suspension. The resulting solution was stirred at −78° C. to room temperature of 22 hours. The solution was again cooled to −78° C., and 100 ml of methylene chloride solution of boron tribromide (25 g/200 ml) was added dropwise thereto, followed by stirring at −78° C. to room temperature for 7 hours. After addition of ice, the pH of the aqueous layer was adjusted to 7.2 with NaOH solution, and then 3.87 g of NaCN was added. The aqueous layer was separated, concentrated, and purified by chromatography (Diaion HP-20, 2 l; water:methanol=1:0 to 9:1, v/v) to obtain 11.17 g of sodium salt of Compound a. The product was dissolved in 80 ml of water, and hydrochloric acid was added thereto to adjust the pH to 3.5. The precipitate formed was separated by filtration and dried to obtain 10.4 g (76.6%) of Compound a.

$^1$H NMR (D$_2$O, NaOD, PD=9.3): 7.13(m, 1h), 6.75(m, 2H), 4.24(d, 1H, J=2.7 Hz), 4.13(m, 1H), 3.70(m, 2H), 3.57(m, 1h), 3.51(bs, 1H), 3.10(dd, 1H, J=10.0, 5.4 Hz), 2.40-2.84(m, 4H), 2.22(s, 3h), 2.03(dd, 1H, J=10.5, 13.2 Hz)

SIMS: 344 (M+1)+

$^{13}$C NMR (D$_2$O, NaOD, PD=9.3): 184.4, 154.6, 138.6, 128.9, 121.9, 120.1, 119.7, 114.8, 70.7, 65.0, 65.0, 58.6, 45.3, 41.9, 33.3, 30.0

REFERENCE EXAMPLE 2

Synthesis of Compound b

Compound a obtained in Reference Example 1 (8 g) was dissolved in 133 ml of chloroform and 36 ml of methanol. 25 ml of chloroform solution of diphenyldiazomethane (5.42 g) was added thereto and the mixture was stirred at room temperature. After one hour and 40 minutes, 20 ml of chloroform solution of diphenyldiazomethane (4.53 g) was further added. After stirring for one hour, acetic acid was gradually added to the reaction mixture until the reddish violet color thereof disappeared. The mixture was diluted with chloroform, washed with saturated NaHCO$_3$ solution and saturated sodium chloride solution, and dried over anhydrous sodium sultate. Then, the solvent was evaporated under reduced pressure, and the residue was purified by chromatography (Wako-gel C-200, 500 ml; hexane:ethyl acetate=2:1) to obtain 10.2 g (86%) of Compound b.

$^1$H NMR (CDCl$_3$): 7.33(m, 10H), 6.97(m, 1H), 6.88(s, 1H), 6.63(m, 2H), 4.18(m, 1H), 3.93(d, 1H), 3.65(m, 2H), 3.44(bs, 1H), 3.38(m, 1H), 3.19(dd, 1H), 3.02(m, 1H), 2.47-2.83(m, 3H), 2.11(s, 3H), 1.93(dd, 1H)

SIMS: 510 (M+1)+

REFERENCE EXAMPLE 3

Synthesis of Compound c

Compound b obtained in Reference Example 2 (1.43 g) was dissolved in 80 ml of acetonitrile, and 10 ml of 1N sodium acetate solution and 80 ml of water were added thereto. 1.5 g of Fremy's salt was added and the mixture was stirred at room temperature. After one hour, 1.5 g of Fremy's salt, 80 ml of water and 20 ml of acetonitrile were added and stirring was continued. After one hour and 20 minutes, 750 mg of Fremy's salt was added and the mixture was stirred, and after one hour and 20 minutes, 750 mg of Fremy's salt was further added, followed by stirring for further one hour and 20 minutes. The reaction mixture was extracted with ethyl acetate, washed with saturated sodium chloride solution and dried over anhydrous sodium sulfate. Then, the solvent was evaporated under reduced pressure to obtain 1.57 g of a crude product. The product was purified by chromatography (Wako-gel C-200, 220 ml; chloroform:methanol=1:0 to 50:1) to obtain 1.16 g (78.8%) of Compound c. In addition, 127 mg (8.9%) of the starting compound (Compound b) was recovered.

$^1$H NMR (CDCl$_3$): 7.25-7.43(m, 10H), 6.89(s, 1H), 6.72(s, 2H), 3.87-4.03(m, 2H), 3.73(m, 2H), 3.52(bs, 1H), 3.45(m, 1H), 2.50-3.23(m, 4H), 2.12-2.33(m, 1H), 2.14(s, 3H), 1.93(dd, 1H)

SIMS: 526 (M+3)+

REFERENCE EXAMPLE 4

Synthesis of Compound d

Compound c obtained in Reference Example 3 (250 mg) was dissolved in 8 ml of acetonitrile, and 8 ml of acetate buffer solution (pH 4.0) was added thereto. 94 mg of sodium azide was added and the mixture was stirred at room temperature for one hour and 30 minutes. Then, 386 mg of Fremy's salt and 3 ml of water were added and stirring was continued. After 2 hours, 120 mg of Fremy's salt was added and the mixture was further stirred at room temperature for one hour and 10 minutes. The crystals formed were filtered under reduced pressure, washed with water, and then dried under reduced pressure to obtain 183 mg (68.0%) of Compound d.

$^1$H NMR (CDCl$_3$): 7.20-7.47(m, 10H), 6.88(s, 1H), 6.23(s, 1H), 3.98(m, 2H), 3.77(m, 2H), 3.51(bs, 1H), 3.47(m, 1H), 2.5-3.3(m, 4H), 2.10-2.35(m, 1H), 2.13(s, 3H, 1.93(m, 1H)

SIMS: 567 (M+3)+

IR$\nu_{max}$ (KBr): 3450, 2110, 1726, 1657, 1636, 1596

REFERENCE EXAMPLE 5

Synthesis of Compound e

Compound c obtained in Reference Example 3 (600 mg) was dissolved in 30 ml of methanol, and 230 mg of copper acetate and 80 μl of triethylamine were added thereto. The mixture was stirred in an atmospere of oxygen at room temperature for 10 days. 20 ml of acetate buffer solution (pH 4.0) was added, and the methanol was evaporated under reduced pressure. The residue was extracted with ethyl acetate, washed with saturated sodium chloride solution and dried. Then, the solvent was evaporated under reduced pressure to obtain 710 mg of a crude product. The product was purified by chromatography (Wako-gel C-200, 60 ml; n-hexane:ethyl acetate=3:2 to 1:1) to obtain 356 mg (56.1%) of Compound e. In addition, 133 mg (22.1%) of the starting compound (Compound c) was recovered.

$^1$H NMR (CDCl$_3$): 7.23-7.43(m, 10H), 6.88(s, 1H), 5.89(s, 0.6H), 5.85(s, 0.4H), 3.87-4.03(m, 2H), 3.79(s, 3H), 3.70(m, 2H), 3.50(bs, 1H), 3.45(m, 1H), 3.15(dd, 1H), 2.50-3.00(m, 3H), 2.13-2.33(m, 1H), 2.13(s, 3H), 1.93(m, 1H)

SIMS: 556 (M+3)+

REFERENCE EXAMPLE 6

Synthesis of Compounds f and g

Compound e obtained in Reference Example 5 (600 mg) was dissolved in 10 ml of acetonitrile and 10 ml of water. 0.12 ml of ethanethiol was added thereto and the mixture was stirred at room temperature. After 30 minutes, 0.12 ml of ethanethiol was further added and stirring was continued. After 2 hours, 3 ml of acetate buffer solution (pH 4.0) was added and the mixture was further stirred at room temperature for 17 hours. Then, 580 mg of Fremy's salt was added, followed by stirring at room temperature for 40 minutes. After the excess ethanethiol was evaporated under reduced pressure, water was added and the resulting reaction mixture was extracted with ethyl acetate. The extract was washed with phosphate buffer solution (pH 7.7) and saturated sodium chloride solution and dried over anhydrous sodium sulfate. Then, the solvent was evaporated under reduced pressure to obtain 630 mg of a crude product. The product was purified by chromatography (Wako-gel C-200, 100 ml; n-hexane:ethyl acetate=4:1 to 2:1) to obtain 143 mg (21.5%) of Compound f and 221 mg (33.3%) of Compound g.

Compound f
  SIMS: 616 (M+3)+
Compound g
  SIMS: 616 (M+3)+

REFERENCE EXAMPLE 7

Synthesis of Compounds h and i

Compound e obtained in Reference Example 5 (1.2 g) was dissolved in 20 ml of acetonitrile. 5 ml of acetate buffer (pH 4.0) and 1.0 ml of i-propanethiol were added, and the mixture was stirred at room temperature for 24 hours. Then, 1.69 g of Fremy's salt, 20 ml of water and 10 ml of acetonitrile were added, and the resulting mixture was stirred at room temperature for three hours and forty minutes. After excess i-propanethiol was evaporated, the residue was extracted with ethyl acetate, and the extract was washed with saturated sodium chloride solution and dried over anhydrous sodium sulfate. The solvent was evaporated to obtain 1.24 g of a crude product. The product was purified by chromatography (Wako-gel C-200, 100 ml; n-hexane:ethyl acetate=4:1 to 2:1) to obtain 391 mg (28.7%) of Compound h and 629 mg (46.2%) of Compound i.

Compound h
  EIMS: 627 (M+), 629 (M+2)+, 598
Compound i
  EIMS: 627 (M+), 629 (M+2)+, 598

REFERENCE EXAMPLE 8

Injection

A distilled water was added to 0.1 g of Compound 3 and 50 g of glucose to make a solution of one liter. The resulting solution was filtered through a membrane filter having a pore diameter of 0.22μ (FGLD 14200, Milli-Pore Co.) with nitrogen gas under pressure (0.5 kg/cm$^2$). The filtrate was put in 20 ml-white ampules in 10 ml portions and sealed in a conventional manner, whereby injections were obtained.

What is claimed is:

1. Compounds represented by the following formula or by the corresponding hydroquinone type formula:

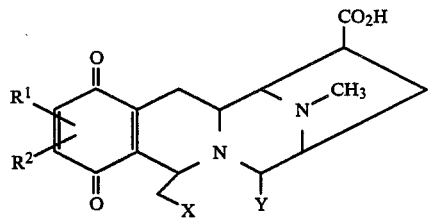

wherein $R^1$ and $R^2$ are independently selected from the group consisting of hydrogen, $C_{1-4}$ alkoxy, azido, amino, $C_{1-3}$ alkylamino, $C_{1-3}$ d-alkylamino, cyclic amino having from 3 to 6 ring members consisting of one nitrogen atom and the rest carbons $C_{1-4}$ alkylthio, and optionally substituted arylthio selected from the group consisting of phenylthio, p-fluorophenylthio and p-methoxyphenylthio; and X is hydroxyl and Y is cyano or X and Y together represent —O— in the form of —X—Y—.

2. Compounds according to claim 1, wherein $R^1$ and $R^2$ are independently alkylthio.

* * * * *

UNITED STATES PATENT AND TRADEMARK OFFICE
CERTIFICATE OF CORRECTION

PATENT NO. : 4,822,882
DATED : April 18, 1989
INVENTOR(S) : HIROMITSU SAITO, ET AL.   Page 1 of 3

It is certified that error appears in the above-identified patent and that said Letters Patent is hereby corrected as shown below:

Title page:

IN [30] FOREIGN APPLICATION PRIORITY DATA

```
"Japan ..... 235858    should    --Japan ..... 61-235858
 Japan ..... 287212    read      --Japan ..... 61-287212
 Japan ..... 207180"             --Japan ..... 62-207180--.
```

IN [57] ABSTRACT

Line 3 from the bottom, "represents" should read --represent--.

COLUMN 11

Line 60, "100 mi;" should read --100 ml;--.

COLUMN 15

Line 28, "J;32 9.7," should read --J=9.7--.

COLUMN 16

Line 2, "J;32 10.7" should read --J=10.7--.
Line 27, "71.9," should read --71.0,--.

COLUMN 17

Line 55, "EXAMPLE 19 CL Synthesis of Compound 20" should read
--          EXAMPLE 19
   Synthesis of Compound 20--.

UNITED STATES PATENT AND TRADEMARK OFFICE
CERTIFICATE OF CORRECTION

PATENT NO. : 4,822,882
DATED : April 18, 1989
INVENTOR(S) : HIROMITSU SAITO, ET AL.    Page 2 of 3

It is certified that error appears in the above-identified patent and that said Letters Patent is hereby corrected as shown below:

COLUMN 19

Line 39, "SIMS:535 (M+3)$^+$" should read --SIMS:536 (M+3)$^+$--.
    Line 65, "temperatur" should read --temperature--.

COLUMN 23

Line 14, "7.13(m, 1h)," should read --7.13(m, 1H),--.
    Line 16, "3.57(m, 1h)," should read --3.57(m, 1H),--.
    Line 17, "2.22(s, 3h)," should read --2.22(s, 3H),--.

COLUMN 24

Line 27, "3H," should read --3H),--.
    Line 37, "atmospere" should read --atmosphere--.

UNITED STATES PATENT AND TRADEMARK OFFICE
CERTIFICATE OF CORRECTION

PATENT NO. : 4,822,882
DATED : April 18, 1989
INVENTOR(S) : HIROMITSU SAITO, ET AL.     Page 3 of 3

It is certified that error appears in the above-identified patent and that said Letters Patent is hereby corrected as shown below:

COLUMN 26

Line 28, "$C_{1-3}$ d-alkylamino," should read --$C_{1-3}$ di-alkylamino,--.
Line 30, "carbons" should read --carbons,--.

Signed and Sealed this

Third Day of October, 1989

Attest:

DONALD J. QUIGG

Attesting Officer                Commissioner of Patents and Trademarks